United States Patent [19]

Schubart et al.

[11] 4,270,998

[45] Jun. 2, 1981

[54] PROCESS FOR THE PREPARATION OF OPTIONALLY SUBSTITUTED ACETONITRILES MONOHALOGENATED IN THE α-POSITION

[75] Inventors: Rüdiger Schubart, Berg.-Gladbach; Rudolf Braden, Odenthal, both of Fed. Rep. of Germany

[73] Assignee: Bayer Aktiengesellschaft, Leverkusen, Fed. Rep. of Germany

[21] Appl. No.: 78,989

[22] Filed: Sep. 26, 1979

[30] Foreign Application Priority Data

Oct. 11, 1978 [DE] Fed. Rep. of Germany ....... 2844200
Feb. 10, 1979 [DE] Fed. Rep. of Germany ....... 2905082

[51] Int. Cl.³ .............................................. B01J 19/12
[52] U.S. Cl. .............................................. 204/158 HA
[58] Field of Search ................................ 204/158 HA

[56] References Cited
FOREIGN PATENT DOCUMENTS 1065405 9/1959 Fed. Rep. of Germany ... 204/158 HA
46-11489 3/1971 Japan ................................ 204/158 HA

*Primary Examiner*—Howard S. Williams
*Attorney, Agent, or Firm*—Sprung, Felfe, Horn, Lynch & Kramer

[57] ABSTRACT

A process for the preparation of an optionally substituted acetonitrile monohalogenated in the α-position which comprises contacting an excess of an optionally substituted acetonitrile of the formula $$R—CH_2—CN$$

wherein
R denotes hydrogen, aliphatic or aryl continuously at an elevated temperature with halogen under the action of light containing UV radiation, the halogenation being carried out to an extent such that the concentration of the acetonitrile monohalogenated in the α-position in the reaction mixture continuously withdrawn from the reaction zone is not more than 33 mole percent, based on the number of mols of all the substances contained in the reaction mixture so withdrawn.

9 Claims, 1 Drawing Figure

PROCESS FOR THE PREPARATION OF OPTIONALLY SUBSTITUTED ACETONITRILES MONOHALOGENATED IN THE α-POSITION

BACKGROUND OF THE INVENTION

1. Field of the Invention

The present invention relates to a process for the selective preparation of optionally substituted acetonitriles monohalogenated in the α-position.

2. Discussion of the Prior Art

It is known to obtain thrichloroacetonitrile by the action of chlorine on acetonitrile in the presence of iodine (Ber.dtsch.chem.Ges. 9, 1594 (1876)). It is further known to react chlorine and acetonitrile at 435° to 440° C. in the vapour phase on a silver-containing catalyst or at 65° C. in the liquid phase whilst irradiating with UV light, to give trichloroacetonitrile (Houben-Weyl, Methoden der organischen Chemie (Methods of Organic Chemistry), Volume V/3, page 634, Georg Thieme Verlag, Stuttgart, 1962). It has also been stated that chlorine in the gas phase does not act on acetonitrile at the boiling point of acetonitrile. The chlorination takes place only above 350° C. (Bull. Soc. Chim. Belges 61, 366 (1952)). It is know to react acetonitrile and chlorine in a ratio of 0.5–0.6:1 in the gas phase at 325° to 380° C. on quartz, active charcoal or perlite to give monochloroacetonitrile in a yield of 75% of the theoretical yield, with conversions of between 90 and 100% (Khim. Prom-st'. (Moscow) 53, 662 (1977)). All of these processes have disadvantages due to the low selectivity and/or the fact that the reactions are carried out at high temperature.

SUMMARY OF THE INVENTION

A process for the preparation of, optionally substituted, acetonitriles, monohalogenated in the α-position has now been found, which comprises continuously contacting an excess of an optionally substituted acetonitrile of the formula

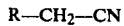

$$R-CH_2-CN \qquad (I)$$

in which

R denotes hydrogen, alkyl or aryl, at elevated temperature with a halogen, under the action of light containing UV radiation and optionally in the presence of a halide of an element of group III to VI of the Mendeleeff periodic table of the elements, the halogenation being carried out to an extent such that the concentration of the acetonitrile monohalogenated in the α-position in the reaction mixture continuously withdrawn from the reaction space is not more than about 33 mol %, based on the number of mols of all of the substances contained in the reaction mixture.

Aliphatic radicals which may be mentioned include for example, a straight-chain, branched or cyclic aliphatic hydrocarbon radical with 1 to 10 carbon atoms including in particular alkyl radicals such as methyl, ethyl, propyl, isopropyl, butyl, isobutyl, hexyl, isohexyl, octyl, isooctyl, decyl and isodecyl and cycloalkyl radicals of 5 to 8 carbon atoms, e.g.cyclopentyl, methyl-cyclopentyl, cyclohexyl, methyl-cyclohexyl, cycloheptyl or methyl-cycloheptyl. Hydrocarbons with 1 to 4 carbon atoms, for example methyl, ethyl, propyl, isopropyl, butyl or isobutyl are preferred.

Aryl which may be mentioned is, for example, an aromatic radical with 6 to 14 carbon atoms, such as phenyl, naphthyl or anthryl. Preferred aryl is the phenyl radical.

Of course, the aliphatic radical and/or the aryl radical can carry one or more substituents which are inert under the reaction conditions, for example halogen, $C_1-C_6$-alkyl, $C_1-C_6$-alkoxy, nitro, chlorosulphonyl or cyano. Examples of halogen which may be mentioned are: fluorine, chlorine, bromine or iodine, preferably fluorine, chlorine or bromine. Hydrocarbons with 1 to 4 carbon atoms may be mentioned as alkyl, for example methyl, ethyl, propyl, isopropyl, butyl or isobutyl. Radicals of lower alcohols with 1 to 4 carbon atoms may be mentioned as alkoxy, for example methoxy, ethoxy, propoxy, isopropoxy, butoxy or isobutoxy.

By way of example, the following optionally substituted acetonitriles may be mentioned as starting materials for the process according to the invention: acetonitrile, propionitrile, butyronitrile, hexanecarboxylic acid nitrile, octanecarboxylic acid nitrile, decanecarboxylic acid nitrile, benzyl cyanide, ortho-chlorobenzyl cyanide, meta-chlorobenzyl cyanide, para-chlorobenzyl cyanide, ortho-, meta- and para-fluorobenzyl cyanide, ortho-, meta- and para-bromobenzyl cyanide, ortho-, meta- and para-methyl-benzyl cyanide, ortho-, meta- and para-methoxybenzyl cyanide, ortho-, meta- and para-nitro-benzyl cyanide, ortho-, meta- and paracyanobenzyl cyanide and o-, m- and p-chlorosulphonylbenzyl cyanide. An example of the reaction of the substituted acetonitriles with halogen which may be mentioned is the reaction with chlorine or bromine, preferably with chlorine.

An example which may be mentioned of an excess of the starting materials of the formula (I) relative to the halogen is a ratio of 2 to 50 and preferably 3 to 20 mols of acetonitrile of the formula (I) per mol of halogen.

In the process according to the invention, the halogen is introduced in the gaseous form into the reaction space. The halogen can be employed without further diluent, but one can also dilute and gaseous halogen with inert gases, for example with nitrogen or with argon. The proportion of the diluent can amount to up to 90% and preferably 30 to 50% of the halogen/inert gas mixture employed.

The reaction according to the invention is carried out in the presence of light containing UV radiation, for example with irradiation with a high-pressure or low-pressure mercury lamp.

The process according to the invention is carried out at elevated temperature. An example of such a temperature which may be mentioned is a temperature of 60° to 300° C. The preferred temperature range is from 70° to 250° C. and the range from 80° to 150° C. is particularly preferred. In a very particularly preferred variant, the process according to the invention is carried out at the boiling point of the optionally substituted acetonitrile to be reacted.

The process according to the invention can be carried out under normal pressure or excess pressure, preferably under normal pressure.

The halogenation in the process according to the invention is carried out to such an extent that the concentration of the optionally substituted acetonitrile mono-halogenated in the α-position in the reaction mixture which is withdrawn from the reaction space is not more than about 33 mol %, based on the number of mols of all of the substances contained in the reaction mixture. For example, a concentration of 0.1 to 33 mol % and preferably 2-25 mol % may be mentioned.

The process according to the invention can be carried out by reacting the optionally substituted acetonitrile with the halogen on its own.

However, the process according to the invention can also be carried out in the presence of a halide of an element of group III to VI of the periodic table. Examples of such elements which may be mentioned are: boron, aluminium, gallium, silicon, titanium, germanium, tin, lead, zirconium, phosphorus, arsenic, antimony, vanadium, niobium, tantalum, sulphur, selenium, tellurium, chromium, molybdenum and tungsten, preferably gallium, silicon, titanium, germanium, tin, phosphorus, arsenic, antimony and sulphur.

Halides of the said elements which may be mentioned for the process according to the invention are the fluorides, chlorides, bromides, iodides, oxychlorides and oxybromides, preferably the chlorides and bromides. Further halides which may be mentioned by way of example are those which have a vapour pressure of at least 0.05 bar in the region of the reaction temperature of the process according to the invention and which do not decompose in this temperature range. Examples of such halides which may be mentioned are: titanium tetrachloride, silicon tetrachloride, sulphur dichloride, tin tetrachloride, gallium-III chloride, germanium tetrabromide, germanium tetrachloride, phosphorus tribromide, phosphorus trichloride, arsenic trichloride, arsenic tribromide and antimony pentachloride. The use of tin tetrachloride is preferred. The halide is employed in an amount of 0.1 to 20% by weight and preferably 1 to 8% by weight, based on the substituted acetonitrile employed.

It is preferred to carry out the process according to the invention in the presence of a halide of an element of group III to VI of the periodic table.

The process according to the invention is carried out continuously.

The reaction space is preferably so designed that the acetonitrile and the halogen are mixed well. For example, the reaction space can have inserts, such as baffles or static mixers, or can be designed as a Venturi tube. However, the halogen can also be introduced via a frit or an annular nozzle into the acetonitrile which is flowing by, if the latter is to be reacted in the liquid phase.

The reaction mixture can be worked up by customary measures, for example distillation, crystallization or absorption, preferably by distillation. The end product obtainable from the working up can subsequently be further purified, for example by fractional distillation. During working up, the optionally substituted acetonitrile employed in excess and the halide described above can be recovered and re-employed in the process according to the invention.

The process according to the invention is generally carried out by introducing the acetonitrile, which is in excess relative to the halogen, and the halogen into the reaction space and reacting them in this space under the action of light containing UV radiation and optionally in the presence of a halide of an element of group 3. to 6. of the Mendeleeff periodic table of the elements, in the temperature range according to the invention. The halide of an element can be introduced into the reaction space separately or as a mixture with the acetonitrile.

The reaction temperature, the level of the molar excess of the optionally substituted acetonitrile, relative to the halogen, the residence time of the reaction mixture in the reaction space and also the presence of the halide described above, which is optionally possible according to the invention, are so chosen, depending on the reactivity of the starting materials, that the halogen is virtually completely converted in the reaction space. The reaction mixture is removed continuously from the reaction space and worked up by distillation.

In the process according to the invention one can prepare compounds of the formula

in which

R denotes hydrogen, alkyl or phenyl and

Hal represents chlorine or bromine, for example: monochloroacetonitrile, monobromoacetonitrile, α-chloro-propionitrile, α-bromo-propionitrile, α-chlorobutyronitrile, α-bromo-butyronitrile, α-chloro-hexanecarboxylic acid nitrile, α-chloro-octanecarboxylic acid nitrile, α-chloro-decanecarboxylic acid nitrile, α-chlorobenzyl cyanide, α-bromo-benzyl cyanide, α-chloro-benzyl cyanides substituted in the nucleus and α-bromo-benzyl cyanides substituted in the nucleus.

The substituted acetonitriles monohalogenated in the α-position which can be prepared by the process according to the invention, and especially monochloroaceonitrile, are obtained in high yields of above 90% of the theoretical yield, based on converted acetonitrile, and in especially high purity, so that they can be employed for many applications without further purification.

The substituted acetonitriles monohalogenated in the α-position which can be prepared by the process according to the invention can be employed as intermediate products for the preparation of plant protection agents, vulcanization accelerators, dyestuffs and medicaments. In particular, monochloroacetonitrile is required for the synthesis of tetrachloropyrimidine (DT-AS (German Auslege schrift No. 1,670,854), which is an important starting material for the preparation of reactive dyestuffs.

As a result of the recycling, according to the invention, of the uncoverted acetonitrile (I), which is separated off from the reaction mixture after leaving the reaction space, high conversions can be achieved without interrupting the process.

As a result of the recycling, according to the invention, of the halide of an element of group III to VI of the periodic table, which is optionally employed, particularly economical use of this auxiliary is possible.

It is surprising that, despite the strong activation of the α-position by the nitrile group, monohalogenation of the α-position can be achieved selectively and with high conversions by the process according to the invention.

BRIEF DESCRIPTION OF DRAWING

Referring to the annexed drawing, the same is a side elevation, partially in section, showing an apparatus suitable for practicing the invention.

EXAMPLES (A) Reaction apparatus

Figure 1:
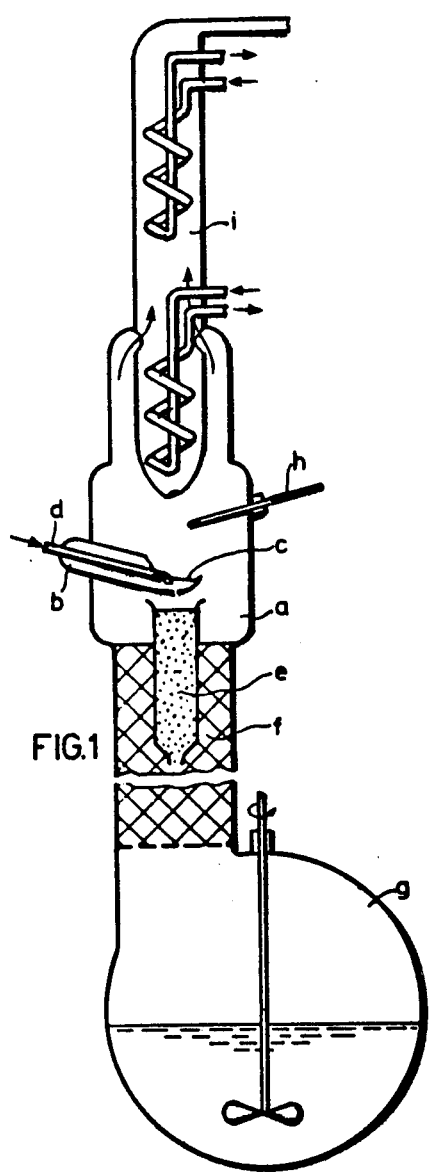

The reaction appartus shown in the FIGURE is used in the examples which follow. The apparatus consists of a vaporizing vessel (g), which contains the optionally substituted acetonitrile and the halide employed. A column (f) which is filled with packing and into which an empty tube (e) which narrows towards the bottom is inserted, is fitted on top of the vaporizing vessel (g). The reaction space (a), in which a device (b) is inserted, in which that portion located in the reaction space is designed as a recess (c), is located above the column (f). The halogen is fed from the outside through the inlet (d) into the device (b) to the recess (c) and at the same time the reaction space is irradiated with UV light. The thermometer (h) is also inserted in the reaction space (a) to check the reaction temperature.

The condenser (i) is so arranged above the reaction space that the liquid components which condense here can drip into the recess (c).

(B) Halogenation 200 g of acetonitrile and 5 g of tin tetrachloride are reacted with chlorine in the apparatus described under A), close to the boiling point of the acetonitrile. The supply of heat to the vaporizing vessel is so controlled that the amount of acetonitrile which refluxes from the condenser (i) into the recess (c) is about 400 g/hour (abut 9.8 mols/hour). After reflux of the acetonitriles has started, chlorine vapour is fed in an amount of about 35 g/hour (about 0.49 mol/hour) through the inlet (d) into the recess (c). The reaction mixture flows through the hole in the recess (c) into the tube (e). The chlorination is discontinued when the conversion is 80%. According to analysis by gas chromatography, the product mixture in the vaporizing flask contains virtually only monochloro-acetonitrile, in addition to the unconverted acetonitrile.

After fractional distillation, the monochloroacetonitrile with a boiling point of 125° to 126° C.; $n_D^{20} = 1.4222$ was obtained.

What is claimed is:

1. A process for the preparation of momohalogenated acetonitrile which comprises contacting acetonitrile with halogen at elevated temperatures in the liquid phase under the action of UV light in the presence of a halide of an element of group III–VI of the Mendeleeff Periodic Table, said halide having a vapor pressure of at least 0.05 bar, the halogenation being carried out to an extent such that the concentration of the acetonitrile monohalogenated in the α position in the reaction mixture continuously withdrawn from the reaction zone is not more than 33 mol percent, based on the number of mols of all the substances contained in the reaction mixture so withdrawn.

2. A process according to claim 1, wherein the process is conducted continuously and excess acetonitrile contained in the reaction mixture withdrawn from the reaction zone is recycled to the reaction zone.

3. A process according to claim 1, wherein there is 1 to 20 mol percent, based on said acetonitrile, of the said halide in the reaction zone.

4. A process according to claim 1 wherein the reaction is carried out in the presence of a halide which is volatile in the temperature range of the reaction and does not decompose.

5. A process according to claim 1 wherein the reaction is carried out in the presence of tin tetrachloride.

6. A process according to claim 1 wherein R denotes hydrogen.

7. A process according to claim 1 wherein R denotes an aliphatic hydrocarbon radical of 1 to 10 carbon atoms.

8. A process according to claim 1 wherein R denotes a $C_1$ to $C_{10}$ alkyl or $C_5$ to $C_8$ cycloalkyl radical which can be substituted by one or more substituents of the group halogen, $C_1$ to $C_6$ alkyl, $C_1$ to $C_6$ alkoxy, nitro, chlorosulfonyl or cyano.

9. A process according to claim 1 wherein R denotes a $C_6$ to $C_{14}$ aryl group which can be substituted by one or more substituents of the group of halogen, $C_1$ to $C_6$ alkyl, $C_1$ to $C_6$ alkoxy, nitro, chlorosulfonyl and cyano.

* * * * *